United States Patent
Harkin

(10) Patent No.: US 6,628,810 B1
(45) Date of Patent: Sep. 30, 2003

(54) HAND BIOMETRICS SENSING DEVICE

(75) Inventor: Gerard F. Harkin, Brighton (GB)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 09/037,105

(22) Filed: Mar. 9, 1998

(30) Foreign Application Priority Data

Mar. 13, 1997 (GB) ............................................. 9705267

(51) Int. Cl.$^7$ ................................................ G06K 9/28
(52) U.S. Cl. ...................................... 382/116; 382/124
(58) Field of Search ............................... 382/115, 116, 382/119, 124–127; 356/71; 340/825.34, 5.53, 5.83; 707/6, 9; 713/186; 902/3, 6

(56) References Cited

U.S. PATENT DOCUMENTS

| | | | |
|---|---|---|---|
| 3,648,240 A | * 3/1972 | Jacoby et al. | ........... 382/115 |
| 4,202,120 A | * 5/1980 | Engel | ........... 340/146.3 E |
| 4,394,773 A | * 7/1983 | Ruell | ........... 382/124 |
| 4,792,226 A | 12/1988 | Fishbine et al. | ........... 356/71 |
| 5,270,711 A | 12/1993 | Knapp | |
| 5,325,442 A | 6/1994 | Knapp | |

FOREIGN PATENT DOCUMENTS

WO    WO9740744    11/1997    ........... A61B/5/117

OTHER PUBLICATIONS

"Novel Fingerprint Scanning Arrays Using Polysilicon TFTs on Glass and Polymer Substrates" by N.D. Young et al, Published in IEEE Electron Device Letters, vol. 18, No. 1, Jan. 1997.

* cited by examiner

Primary Examiner—Brian Werner

(57) ABSTRACT

A hand biometrics sensing device includes an array of sensing elements (12) defining a sensing area (11) over which a person's hand is placed and which has a first portion (14) in which the sensing elements are arranged to provide high resolution sensing suitable for sensing fingerprint patterns and a second portion (15) in which the sensing elements are arranged to provide lower resolution sensing suitable for sensing at least one other hand biometric characteristic, for example, hand geometry, finger length, width or inter-joint dimensions. The sensing elements, which may include sense electrodes (17) connected to switching devices (16) such as TFTs, are arrayed in rows and columns and addressed by peripheral drive circuits via sets of row and column address conductors (18, 20), resulting in a low-cost, compact device.

2 Claims, 3 Drawing Sheets

HAND BIOMETRICS SENSING DEVICE

The present invention relates to a sensing device for sensing a biometric characteristic of a person's hand, and comprising a matrix array of sensing elements defining a sensing area.

The use of biometric sensing and hand biometric sensing in particular as a method of verifying the identity of a person is well known. One example of a hand biometric sensing device is a fingerprint sensor.

Fingerprint sensing systems are attracting considerable interest for many different applications, ranging from high security uses such as access control for buildings and computers to low level security uses such as replacements for conventional locks and keys. Their main advantages for such purposes are that they are relatively easy and convenient to use, they avoid the need for keys, personal identification numbers and the like, and should be less susceptible to fraudulent use. The need for improving security and preventing fraudulent use, particularly, for example, when conducting financial transactions using banking terminals and ATMs and especially new applications arising from computer networking which include home banking and shopping on the internet, is widely recognised.

Examples of fingerprint sensing devices using matrix arrays of sensing elements are described in U.S. Pat. No. 5,325,442 (PHB 33628) and in the paper by N. D. Young et al entitled "Novel Fingerprint Scanning Arrays Using Polysilicon TFTs on Glass and Polymer Substrates" published in IEEE Electron Device Letters, Vol. 18, No. 1, January 1997. In these devices a capacitive sensing approach is utilised. The sensing elements are arranged in a two dimensional, row and column, planar array, occupying an area generally corresponding to the size of a fingertip, and addressed by sets of row and column address conductors. Each sensing element includes a sense electrode which together with an overlying part of a person's finger and an intervening layer of insulator material, that provides a sensing surface on which the finger is placed, constitutes a capacitor. Charging of the sensing element capacitors, using signals applied to the address conductors, is controlled by switching devices in the form of thin film transistors (TFTs) in the sensing elements. The individual capacitances of these capacitors depend on the spacing of the sense electrodes from the overlying fingerprint portions so that ridges and valleys of a fingerprint produce different capacitances. By measuring the charge storage characteristics of the capacitors in the sensing elements an indication of the presence of a ridge or valley above each sensing element is obtained. The rows of sensing elements are addressed one at a time in turn so as to scan the fingerprint and the variation in sensed capacitances produced over the array by a fingerprint ridge pattern provides an electronic image or representation of the three dimensional form of the fingerprint surface.

These kinds of sensing devices are fabricated using the same kind of matrix switching thin film technology developed for active matrix display devices and the like to form the array of sensing elements and the sets of address conductors on a common substrate of glass or plastics and are considerably more compact and much less expensive to produce than conventional optical type fingerprint sensing devices which require a prism, lenses, a light source and a CCD chip or CMOS image sensor chip.

It is an object of the present invention to provide an improved sensing device of the kind using a sensing element array which is adapted to offer variable levels of security in use.

According to one aspect of the present invention, there is provided a sensing device as described in the opening paragraph which is characterised in that in a first portion of the array the sensing elements have a resolution capable of sensing the fingerprint pattern of a person's finger when placed over that portion of the sensing area and in a second portion of the array the sensing elements have a lower resolution for sensing at least one other hand biometric characteristic. The ability of the sensing device, with its single sensing element array, to sense not just a person's fingerprint but one or more additional biometric characteristics is important and advantageous. The performance of any hand biometric characteristic sensing system is based on system error rates, namely the false rejection rate and the false acceptance rate. For many applications employing a system which senses just one biometric characteristic the error rate is not satisfactory. By combining two, or more, biometric sensing systems the possibility exists for reducing the overall effective error rate but because most conventional biometric sensing systems tend to be expensive such combinations are not widely used and have been restricted to particular applications which justify the cost. The sensing device of the present invention, however, offers the ability to sense different hand biometric characteristics using just a single sensing element array for this purpose, thus simplifying manufacture and reducing cost. By using thin film technology to fabricate the sensing element array the device offers the advantage of compactness which is important when, for example, the sensing device is to be incorporated in other products, as well as being relatively inexpensive to produce.

The sensing elements may be of the kind described in the aforementioned patent specification and paper which use a capacitive sensing approach and comprise thin film switching devices such as TFTs. However, it is envisaged that sensing elements which are capable of responding to the presence of a hand surface part in proximity thereto in a different manner to provide an indication of hand biometric characteristics could be utilised. For example, the sensing elements may be responsive to pressure or skin resistance such that, in the first portion of the array, the sensing elements respond differently to the ridges and troughs of fingerprint pattern by virtue of the pressure, contact, or electrical resistance caused by the ridges when the finger is pressed over the array.

The other hand biometric characteristic which is sensed can be finger length and/or width, hand geometry, palm print or finger inter—joint dimensions, all of which only demand lower (coarser) sensing resolution for their measurement compared with fingerprint pattern sensing. More than one of these may be sensed if desired. The data representative of the sensed characteristic or characteristics can be utilised together with the sensed fingerprint data to improve the accuracy of verification by comparing, with stored data, not just fingerprint information but this additional data as well. In practice, the biometric characteristics to be sensed could be selected depending on the level of security required, and the fingerprint sensing capability need not always be used. For low—level security purposes, finger length/width or finger inter—joint lengths may be sufficient whereas for high level security applications more than two biometric characteristics may be used, one preferably being fingerprint data.

By using a suitable stylus, adapted to interact with the sensing elements, the sensing elements could be utilised to detect dynamic movement of the stylus, thus enabling the device to be used also for scanning a person's signature pattern for additional security.

The overall dimensions of the sensing element array will vary according to the particular characteristics to be sensed. An array adapted to sense only finger characteristics would, of course, be considerably smaller overall than an array for sensing hand geometry and could, for example, be conveniently incorporated in a smart card. In any event, the use of thin film technology enables differently sized arrays to be fabricated relatively easily. The provision of comparatively high and low resolution regions in the array leads to benefits both in manufacture and operation. In particular, fabrication is simplified, resulting in better manufacturing yields, the array can be driven at faster scanning rates, and the amount of drive circuitry needed to address the sensing elements will be less than that which would be required by a sensing element array having the same, high, resolution capability throughout.

In a preferred embodiment, the sensing elements of the array are arranged in rows and columns and connected to sets of row and column address conductors, each row of sensing elements being connected to a common row address conductor and addressed in turn by a drive circuit connected to the set of row address conductors, and the pitch of the sensing elements in the column direction, and the spacing between adjacent row address conductors, is greater in the second portion of the array than in the first portion. Such an array can easily and conveniently be fabricated at low cost using thin film technology to form the address conductors and sensing elements on a substrate of, for example, glass or plastics. In the first portion of the array the sensing elements in each column may be connected to a common column address conductor and in the second portion of the array the number of sensing elements in each row is less than in the first portion and the sensing elements are connected to certain ones only of the column address conductors associated with the sensing elements in the first portion, for example every nth column address conductor where n is a whole number greater than one. Where n, for example, equals 8, then the sensing element pitch in the row direction in the second portion will be one eighth of the sensing element pitch in the first portion.

The division of the sensing element array into high and low resolution portions leads to further advantages when using sensing elements of, for example, the kind described in the aforementioned publications. Because the number of sensing elements connected to each column conductor is small compared with that of an array having the same, high, resolution throughout, the parasitic column capacitance is lower which means that the noise performance of the read-out amplifiers connected to the column conductors is improved and signal attenuation is reduced. Also, less noise from the row drive circuit is coupled to the read-out amplifiers through the sensing elements due to the fact that fewer row conductors are needed.

Various other arrangements may be possible. For example, in one alternative arrangement the rows of sensing elements in the first portion may be physically shorter than the rows of sensing elements in the second portion with the column address conductors associated with the sensing elements in the first portion being fanned out at the transition between the two portions and each of these column address conductors being associated with a respective column of sensing elements in the second portion. In this case, the number of sensing elements in each row in both portions is the same and the pitch of the column conductors is constant in both portions but larger in the second portion. In the, first portion, the smaller sensing element pitch provides the resolution necessary for fingerprint sensing, the overall area occupied by the sensing elements in this portion being slightly larger than the overall size of a person's finger tip, while the sensing elements in the second portion, being of larger pitch in both the row and column directions, occupy a considerably larger area, for example conforming with the size of a person's hand. In this arrangement, however, the fanning out of the column address conductors will result in a dead region at the transition between the two portions.

According to another aspect of the present invention, there is provided a hand biometric characteristic recognition system comprising a sensing device in accordance with the one aspect of the present invention, processing means connected to the sensing device for receiving an output from the device indicative of the sensed hand biometric characteristics and comparing such with stored hand biometric characteristics data.

A hand biometric characteristic sensing device in accordance with the present invention, and a recognition system using such, will now be described, by way of example, with reference to the accompanying drawings, in which.

It should be understood that the Figures are merely schematic and are not drawn to scale. The same reference numerals are used throughout the specification to indicate the same or similar parts.

Figure 1:
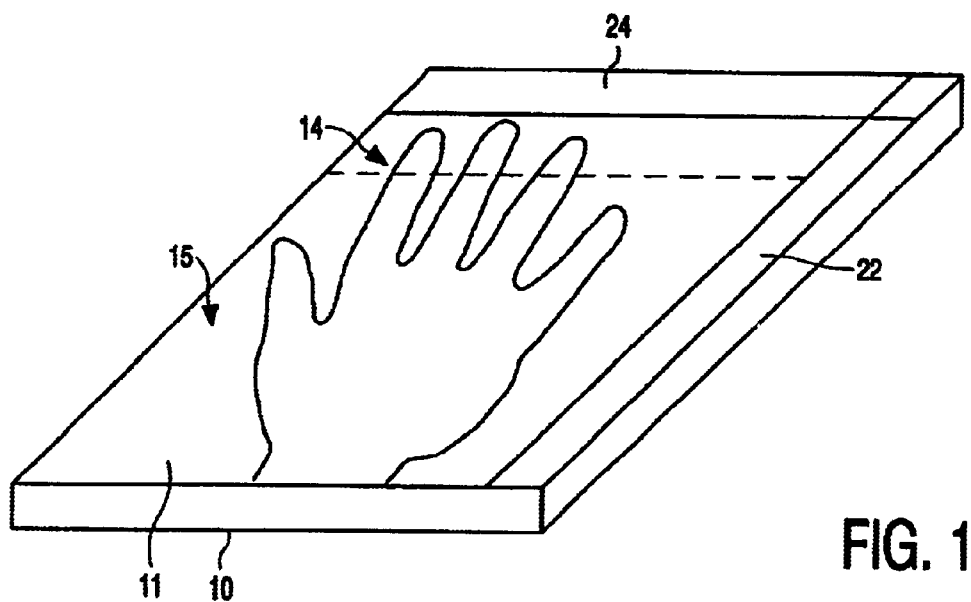
FIG. 1 is a schematic perspective view of an embodiment of the sensing device.

Referring to FIG. 1, the sensing device comprises a panel 10 whose upper side provides a generally rectangular sensing surface 11 upon which hands or fingers whose characteristics are to be sensed are placed. Along two, or more, sides of the sensing area, adjacent the periphery of the panel, addressing circuits 22, 24, for example in the form of ICs, for addressing a two —dimensional, planar array of sensing elements underlying the sensing surface 11, and deriving electrical data output signals of the hand biometric characteristics sensed thereby, are provided. The sensing device is shown here in a simple schematic form. In practice, the panel 10 would be mounted in a housing which encloses the addressing circuits, while leaving the sensing surface 11 exposed, and could either be incorporated in other equipment, for example point of sale terminal, ATM or the like, or provided as a stand-alone unit in which case a cable (not shown) would be included for power supply input and data signal output. The sensing surface 11 is divided into two generally rectangular portions 14 and 15, the first portion 14 occupying a smaller, elongate, region at one end of the array whose height is selected to accommodate finger tips and the second, larger, portion 15 being dimensioned to receive at least a major part of the rest of the hand, as shown in FIG. 1. A guide, not shown, may be provided for positioning the hand appropriately over the surface to prevent rotations. Apart from their dimensions, the two portions differ in that the first portion 14 has a resolution sensing capability sufficient to allow fingerprint patterns to be sensed while the second portion 15 has a comparatively low resolution capability adequate for sensing other, generally large, hand biometric characteristics relating to the profile or outline of hand parts such as finger length and/or width, finger inter—joint distances, the overall shape of a hand, or palm prints.

Figure 2:
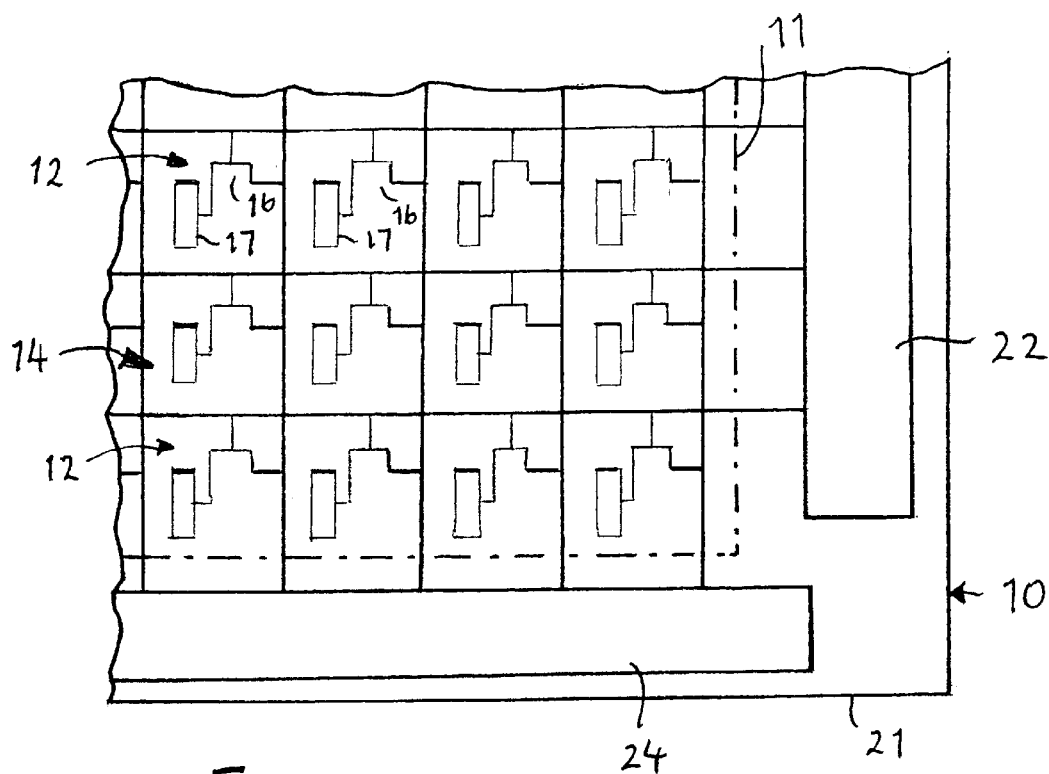
FIG. 2 is a simplified diagram illustrating a part of a sensing element array, and associated drive circuitry, of the device.

The sensing element array of the device comprises an active matrix addressed row and column array of individual, and regularly-spaced, sensing elements 12 and a part of the array, cormprising, for simplicity, sections of just three rows from the higher resolution portion 14 of the array, together with associated drive circuits, is shown in FIG. 2. The sensing elements 12, and the manner in which they operate, are similar to those described in U.S. Pat. No. 5,325,442 to which reference is invited for further information in these respects. Briefly, the sensing elements are addressed by a row drive circuit 22 and a column sense-circuit 24 via sets of row (selection) address conductors 18 and column (sensing) address conductors 20 connected at their ends to these circuits, with individual sensing elements 12 being located at respective intersections of the two address conductor sets. The sensing elements 12 and sets of address conductors are all carried on a common substrate 21. Sensing elements 12 in the same row are connected to a respective one of the row conductors 18 and sense elements in,the same column are connected to a respective one of the column conductors 20. Sensing operation of the elements 12 is capacitive in manner. Each sensing element 12 includes a switching device, comprising here a TET 16, connected between an associated column conductor 20 and a sense electrode 17 and operable by a selection (gating) signal on the row conductor 18 to which it is connected to apply periodically a potential present on the column conductor 20 to the electrode 17. The electrodes 17 of the array of sense elements are covered by a layer of dielectric material whose upper surface provides the sensing surface 11 and together with this layer and an overlying, localised, hand or finger part acting as a ground electrode constitute individual capacitors. The capacitances of these capacitors depend on the spacing of the immediately overlying hand or finger parts, which in the region 14 of the array will be determined principally by the ridges and troughs of a fingerprint while in the region 15 it will be determined more by hand and finger surfaces in contact with, or close to, the sensing surface 11.

Upon applying a potential to the electrodes 17, an amount of charge is stored on these capacitors according to their capacitance values. The row drive circuit 22 addresses each row of sense elements in this manner by applying a selection signal to each row conductor 18 in sequence so as to charge up the capacitance of each row of sensing elements in turn. The charging current for the individual capacitors when they are addressed flows through the column conductors 20 and the amount of this current, indicative of the respective capacitance value, is sensed by means of charge or current sensing read-out amplifiers in the column drive circuit 24. The procedure is repeated for each row to scan the fingers and hand and produce over one complete field an electronic image of the array capacitances representative of the three dimensional profile of fingerprints and proximate hand surfaces from which an indication of the geometry of fingers and the hand can be derived.

Other forms of sensing elements are possible, such as the capacitive sensing elements described in PCT WO97/4Q744. Moreover, other types of sensing elements which rely on a different sensing approach to detect an overlying hand or fingerprint portion can be used. For example, sensing elements responsive to physical contact, by virtue of the skin surfaces physically touching an electrode of the sensing element, or pressure can be used. In U.S. Pat. No. 5,270,711 (PHB 33548) a touch sensing array is described in which each sensing element comprises a switching device, in the form of a TFT or thin film diode, and a capacitor which is periodically charged through the switching device and whose one plate is grounded by touching, either directly or through a deformable, pressure responsive, membrane. By monitoring the charging characteristics of the sensing elements, those which are touched can be identified. With the sensing elements having suitable resolution by being appropriately sized and spaced, such an array could be used for sensing the ridge patterns of fingerprints and hand part shapes.

The sensing element array is conveniently fabricated by the same kind of thin film technology as used for producing other large area, active matrix, arrays such as found in active matrix display devices. Briefly, the method typically involves the deposition and definition by photolithographic processes of a number of layers on a common insulating substrate. The sense electrodes 17 and sets of address conductors can be formed from deposited metal layers and the TFTs 16 may be amorphous silicon or polysilicon type TFTs. The substrate can be of glass, quartz or polymer material. The row and columns drive circuits 22 and 24 may be fully integrated on the same substrate and fabricated simultaneously with array using the same processes, particularly when polysilicon TFTs are used in the array.

Figure 3:
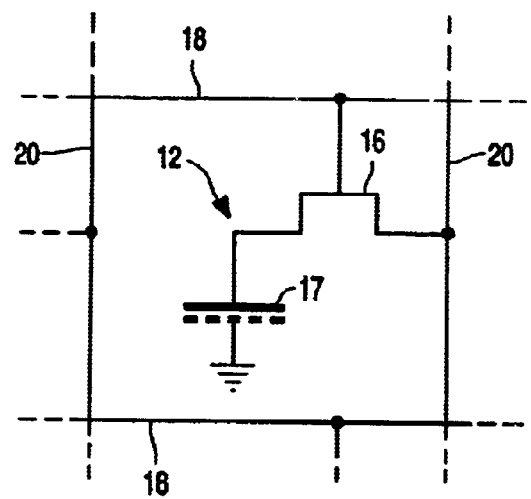
FIG. 3 shows the equivalent circuit of one example of a sensing element in the array.
Figure 4:
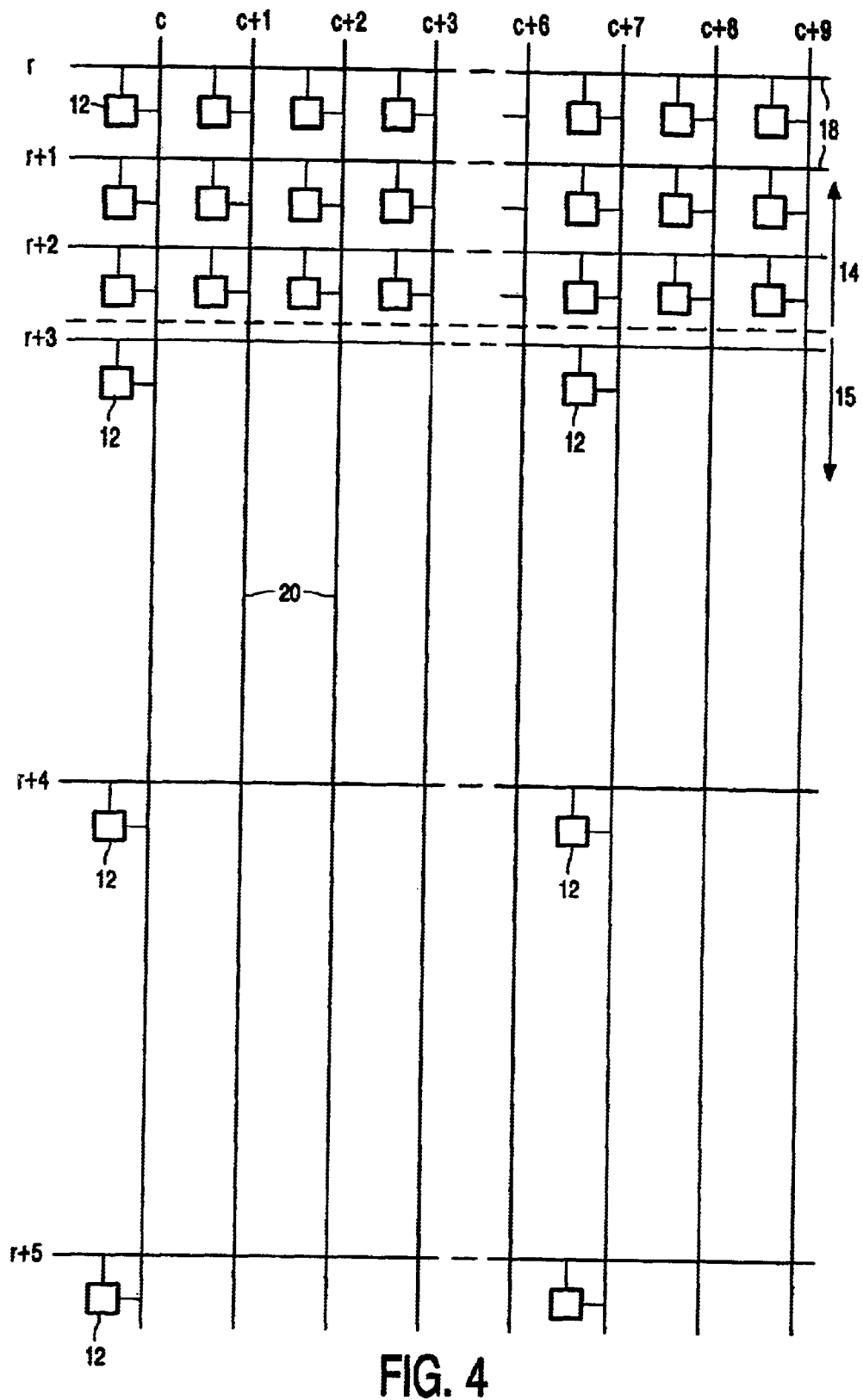
FIG. 4 is a schematic diagram of a part of the array showing typical sensing elements at a transition region between high and low resolution sensing portions of the array.

FIG. 4 illustrates schematically a part of the sensing element array at the transition between the portion 14 and the lower resolution portion 15 and including sections of six successive row conductors 18, r to r+5, and ten successive column conductors 20, c to c+9. The column conductors 20 are regularly spaced at, for example, 50 $\mu$m intervals. The row conductors 18 in the portion 14, i.e. row conductors r to r+2 in FIG. 3, are regularly spaced at, for example, a similar pitch of 50 $\mu$m. The sensing elements 12 in this portion 14 are thus arranged in regularly—spaced rows and columns with a pitch of 50 $\mu$m both vertically and horizontally. The resolution afforded by sensing elements in this portion is, therefore, appropriate to sensing fingerprint minutia. In the region 15, however, the row conductors 18 are spaced at a considerably greater distance apart than in the region 14. The spacing may be, for example, 400 $\mu$m. Furthermore, the sensing elements 12 in this region 15 are provided at a greater horizontal spacing, in this example adjacent every eighth column conductor 20, i.e. the column conductors c and c+7. Thus, the sensing elements in the portion 15 are arranged in regularly—spaced rows and columns at a 400 $\mu$m pitch, both horizontally and vertically. The resolution afforded by the sensing elements in this portion 15 is, therefore, adapted to sense coarser, and larger, biometric characteristics such as finger or hand profiles. If a different column conductor pitch is used, for example 70 $\mu$m, then every sixth column conductor 20 may be utilised for the sensing elements in the second portion. The pitch of the sensing elements in the portion 15 can, of course, be varied as desired.

The sections of the column conductors 20 within the portion 15 which are not utilised by the sensing elements can be omitted if desired. However, arranging them so as to extend the height of the entire array conveniently allows the column sensing circuit 24 to be connected to either end of the array. The sensing element rows in both portions are addressed in similar manner and at the same rate. Thus, the time taken to address the rows r to r+2 is the same as that taken to address rows r+3 to r+5.

By using large area, thin film technology to fabricate this array, a low-cost and comparatively compact sensing device is obtained. The overall size of the sensing element array may be around 25 cms by 15 cms with the first portion 14 occupying an area of approximately 3 cm by 15 cms. In this first portion the sensing elements are responsive to the ridges and troughs of a fingerprint to provide fingerprint ridge patterns information while their outputs provide also an indication of the profile of the fingertips. The sensing elements in the second portion 15 are responsive to overlying hand surface parts to provide an indication of the hand outline and three dimensional surface profile characteristics such as finger joint regions. Upon addressing all sensing element rows, a hand overlying the array is scanned and the response of individual sensing elements detected in the column sense circuit 24 to provide in effect an electronic image of fingerprint patterns and hand geometry characteristics generally. Signals indicative of the individual responses of the sensing elements are provided at an output of the sense circuit 24 in the form of a serial data pulse train, as described in U.S. Pat. No. 5,325,442.

Since fewer sensing elements are connected to a column conductor 20 than would be the case for an array having the same, high, resolution throughout the noise performance of the read-out amplifiers is improved and signal attenuation reduced since parasitic column capacitances are lowered. Also, as fewer row conductors are needed, less noise from the row drive circuit 22 will be coupled to the read-out amplifiers through the sensing elements.

Rather than addressing all the rows of sensing elements in the array in succession, the two portions 14 and 15 may be addressed separately.

Figure 5:
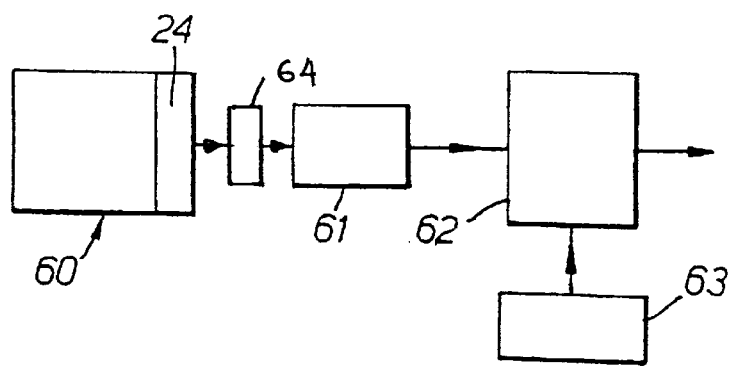
FIG. 5 is a schematic block diagram of a recognition system incorporating the sensing device.

FIG. 5 shows in schematic block form a fingerprint recognition system incorporating the sensing device, here represented by the block 60. The system includes means responsive to the serial pulse train output from the sensing circuit 24 to provide characteristical data of a sensed fingerprint, and other hand biometric characteristic(s), and means for comparing said characteristical data with stored characteristical biometrical data for one or more hands. The output obtained from the sensing device is provided in a form comparable to the video output provided by an image sensor in known optical fingerprint sensing devices. Accordingly, and as will be apparent to skilled persons, components of the system, other than the sensing device, can be generally of the kind employed in systems using optical sensing devices. The fingerprint characteristical data, in accordance with standard practice, may take the form of information regarding the orientation of ridge lines and relative positions of minutiae, that is the ending and bifurcations of the lines. The processing of information obtained from the sensing device to produce and compare characteristical data can follow known schemes and techniques. Because the sensing device of the invention is capable of providing information of the three dimensional profile of a fingerprint improved accuracy of identification or verification can be obtained by making use of topological features in addition to the spatial positions of minutiae, although of course use may be made only of information in respect of the two-dimensional ridge patterns to simplify the processing necessary if less accuracy is acceptable. Briefly, the output from the device 60, suitably conditioned, for example by a thresholding circuit 64, is fed to an analysis circuit 61 which is programmed to identify and extract characterising features of the sensed fingerprint, such as the position of minutiae, and also to extract information representative of other hand biometric characteristics such as finger length or width, finger inter—joint dimension information, palm prints or hand geometry signifying the shape or profile of the hand. Data from the circuit 61 is supplied to a computer 62 which through standard algorithms compares the data with biometric characteristical data of a plurality of hands, or a single hand depending on whether the system is used for identification or merely verification purposes, held in a storage device 63 and which provides an output in accordance with whether or not a match has been found.

The circuit 61 can be programmed either to utilise the three dimensional information for a fingerprint provided by the sensing device for high accuracy of recognition, or alternatively, with appropriate discrimination to select particular output signal values from the device 60, utilising specific information representative of the two dimensional ridge pattern in the nature of a binary image similar to that obtained from known optical sensing devices.

In addition to sensing the physical characteristics of a person's hand, the array can be utilised further as a means for sensing a person's signature to provide the kind of security found in signature recognition systems. To this end a suitable form of stylus, adapted to cause an appropriate response in the sensing elements when in close proximity thereto so as to detect the dynamic movement of the stylus, would be used.

The overall size of the array can be varied depending on which hand biometric characteristics, in addition to fingerprints, are to be sensed. For example, the length of the array can be reduced if merely finger characteristics are to be sensed. If only the fingerprint and a finger biometric characteristic such as finger length, width or inter—joint distances, are required then obviously both the length and width of the array can be considerably reduced and the size of the array need only be such as to accommodate a person's index finger or two fingers for example. A sensing array sized to accommodate just one or two fingers could readily be incorporated in a smart card for example and could conveniently be used to sense a person's signature as well.

The portion 14 may be used for sensing more than one fingerprint of a person's hand. When this is not needed the active sensing region of the array portion 14 may be restricted to a smaller area occupying a part only of the full width of the surface 11 shown in FIG. 1 over which the tip of, for example, a person's index finger is placed, the area to be used for this purpose being suitably marked or defined by a mask on the portion 14.

From reading the present disclosure, other modifications will be apparent to persons skilled in the art. Such modifications may involve other features which are already known in the field of fingerprint and hand sensing and component parts thereof and which may be used instead of or in addition to features already described herein.

What is claimed is:

1. A sensing device for sensing a biometric characteristic of a person's hand and comprising
   a matrix array of sensing elements defining a sensing area, wherein
   in a first portion of the array the sensing elements have a resolution capable of sensing the fingerprint pattern of a person's finger when placed over that portion of the sensing area;
   in a second portion of the array the sensing elements have a lower resolution for sensing at least one other hand biometric characteristic;
   the sensing elements are arranged in rows and columns on a substrate and
   sets of address conductors carried on the substrate for addressing the sensing elements, the rows of sensing elements each being connected to a respective row address conductor, a pitch of the row address conductors in the column direction being greater in the second portion than in the first portion; and a drive circuit, connected to the set of row address conductors, for addressing the rows of sensing elements in turn, wherein in the first portion the sensing elements in each column are connected to a respective column address conductor and in the second portion the number of sensing elements in each row is less than in the first portion and the sensing elements are connected to selected ones only of the column address conductors associated with the sensing elements in the first portion.

2. A hand biometric characteristic recognition system comprising:

a sensing device for sensing a biometric characteristic of a person's hand and comprising a matrix array of sensing elements defining a sensing area, characterised in that in a first portion of the array the sensing elements have a resolution capable of sensing the fingerprint pattern of a person's finger when placed over that portion of the sensing area and in a second portion of the array the sensing elements have a lower resolution for sensing at least one other hand biometric characteristic, processing means connected to the sensing device for receiving an output from the device indicative of the sensed hand biometric characteristics and comparing such with stored hand biometric characteristics data; and a stylus adapted to be sensed by the sensing elements of the array when in proximity thereto so as to enable a person's signature to be sensed when written over the array using the stylus.

* * * * *